(12) United States Patent
Cheekoori

(10) Patent No.: US 11,285,184 B2
(45) Date of Patent: Mar. 29, 2022

(54) CANNABIDIOL ALKALINE COMPOSITION

(71) Applicant: CHIROSYN DISCOVERY TECHNOLOGIES INC., Toronto (CA)

(72) Inventor: Sreedhar Cheekoori, Toronto (CA)

(73) Assignee: CHIROSYN DISCOVERY TECHNOLOGIES INC.

( * ) Notice: Subject to any disclaimer, the term of this patent is extended or adjusted under 35 U.S.C. 154(b) by 0 days.

(21) Appl. No.: 16/483,249

(22) PCT Filed: Apr. 24, 2019

(86) PCT No.: PCT/CA2019/050513
§ 371 (c)(1),
(2) Date: Aug. 2, 2019

(87) PCT Pub. No.: WO2020/041860
PCT Pub. Date: Mar. 5, 2020

(65) Prior Publication Data
US 2021/0330724 A1    Oct. 28, 2021

Related U.S. Application Data

(60) Provisional application No. 62/723,601, filed on Aug. 28, 2018.

(51) Int. Cl.
*A61K 31/352* (2006.01)
*A61K 36/185* (2006.01)
*A61K 9/00* (2006.01)
*A61K 9/16* (2006.01)
(Continued)

(52) U.S. Cl.
CPC .......... *A61K 36/185* (2013.01); *A61K 9/0095* (2013.01); *A61K 9/1617* (2013.01); *A61K 31/05* (2013.01); *A61K 31/352* (2013.01); *A61K 47/44* (2013.01)

(58) Field of Classification Search
CPC .................................................... A61K 31/352
See application file for complete search history.

(56) References Cited

U.S. PATENT DOCUMENTS

2010/0129457 A1\* 5/2010 Razavi ............... A61K 47/6929
424/489

FOREIGN PATENT DOCUMENTS

| CA | 2698752 | 2/2009 |
| CA | 2937471 | 9/2016 |

OTHER PUBLICATIONS

International Searching Authority, Application No. PCT/CA2019/050513; International Seach Report and Written Opinion dated Jul. 3, 2019.

(Continued)

*Primary Examiner* — Benjamin J Packard
(74) *Attorney, Agent, or Firm* — Lavery, De Billy, LLP; Beatrice Ngatcha

(57) ABSTRACT

An aqueous alkaline composition comprising a cannabinoid which may be cannabidiol (CBD) used alone or in combination with other cannabinoids. An alkalizing agent which comprises pico size carbon particles is present in the composition, in an amount suitable for buffering the composition to a pH between about 7.5 and 9.5. The aqueous alkaline composition is stable and may be used in the preparation of a beverage or a pharmaceutical composition.

20 Claims, 2 Drawing Sheets

EIC (m/z 313) of CBD oil

(51) Int. Cl.
 A61K 31/05 (2006.01)
 A61K 47/44 (2017.01)

(56) References Cited

OTHER PUBLICATIONS

Machon et al., "Structural, electronic, and vibrational properties of (4,4) picotube crystals"; Physical Review B 72 155402 (2005).
Hippalgaonkar et al., "Enhanced Solubility, Stability, and Transcorneal Permeability of Delta-8-Tetrahydrocannabinol in the Presence of Cyclodestrins"; PharmSciTech (Jun. 2011), vol. 12, No. 2.
Merrick et al., "Identification of Psychoactive Degradants of Cannabidiol in Simulated Gastric and Physiological Fluid"; Cannabis and Cannabinoid Research (2016), vol. 1.1.
Pertwee, R., "The diverse CB1 and CB2 receptor pharmacology of three plant cannabinoids: Δ9-tetrahydrocannabinol, cannabidiol and Δ9-tetrahydrocannabivarin"; British Journal of pharmacology (2008), 153(2), 199-215.
Long et al., "A behavioral comparison of acute and chronic Δ9-tetrahydrocannabinol and cannabidiol in C57BL/6JArc mice"; International Journal of Neuropsychopharmacology (2010), 13(7), 861-876.
Batalla et al., "Neuroimaging studies of acute effects of THC and CBD in humans and animals: a systematic review"; Current Pharmaceutical Design (2014), 20(13), 2168-2185.
Sultan et al., "A systematic review and meta-analysis of the haemodynamic effects of Cannabidiol"; Frontiers in Pharmacology (2017), 8, 81.
Watanabe et al., "Conversion of cannabidiol to Δ9-tetrahydrocannabinol and related cannabinoids in artificial gastric juice, and their pharmacological effects in mice"; Forensic Toxicology (2007), 25(1), 16-21.
Trofin et al., "Long-term storage and cannabis oil stability"; Revista De Chemie (2012), 63(3), 293-297.
Van Nguyen et al., "Enhanced gastric stability of esomeprazole by molecular interaction and modulation of microenvironmental pH with alkalizers in solid dispersion"; International Journal of Pharmaceutics (2017), 523, 189-202.
Benetti et al., "Esomeprazole immediate release tablets: Gastric mucosa ex vivo permeation, absorption and antisecretory activity in conscious rats"; Journal of Controlled Release (2016), 238, 203-210.
Leuner et al., "Improving drug solubility for oral delivery using solid dispersions"; European Journal of Pharmaceutics and Biopharmaceutics (2000), 50, 47-60.
Park et al., "Modulation of microenvironmental pH and utilization of alkalizers in crystalline solid dispersion for enhanced solubility and stability of clarithromycin"; Acrh Pharm. Res. (2015), 38, 839-848.
Gallily et al., "Overcoming the bell-shaped dose-response of cannabidiol by using cannabis extract enriched in cannabidiol"; Pharmacology & Pharmacy (2015), 6, 75-85.

* cited by examiner

CANNABIDIOL ALKALINE COMPOSITION

CROSS REFERENCE TO RELATED APPLICATIONS

This application claims benefit of U.S. Provisional Patent Application No. 62/723,601, filed on Aug. 28, 2018, the content of which is incorporated herein in its entirety by reference.

FIELD OF THE INVENTION

The present invention relates generally to compositions comprising a cannabinoid. More specifically, the invention relates to an aqueous composition comprising cannabidiol (CBD) and an alkalizing agent which comprises pico size carbon particles.

BACKGROUND OF THE INVENTION

*Cannabis sativa* L. is one of the oldest known medicinal plants and has been extensively studied with respect to its phytochemistry. A *Cannabis* plant extract comprises around 483 identified compounds belonging to various chemical classes. Of these classes, the cannabinoid class comprises unique compounds, known to exist only in *Cannabis sativa* L. There are 66 known plant-derived cannabinoid compounds, the most prevalent of which are Δ-9-tetrahydrocannabinol (THC or Δ-9THC or dronabinol), cannabidiol (CBD) and cannabinol (CBN). Other cannabinoids include cannabigerol (CBG), cannabichromene (CBC) and cannabinodiols (CBND). Cannabidiol (CBD) and Δ-9-tetrahydrocannabinol (THC) are the most researched/studied cannabinoids.

Δ-tetrahydrocannabinol (THC) outlined below has the systematic name (−)-(6aR,10aR)-6,6,9-trimethyl-3-pentyl-6a,7,8,10a-tetrahydro-6H-benzo[c]chromen-1-ol, is a naturally occurring compound and is the primary active ingredient in the controlled substance marijuana. The pharmacological activity of THC is due to its binding to the type 1 cannabinoid protein receptor (CB1) and activation, thus generating biological effects including analgesia, muscle relaxation, anti-emesis, and appetite stimulation. Currently, THC is commercially available in the U.S. as an orally administered soft gelatin capsule under the trade name Marinol® and is indicated for the treatment of anorexia associated with weight loss in patients with AIDS, as well as nausea and vomiting associated with cancer chemotherapy in patients who have failed to respond adequately to conventional antiemetic treatments.

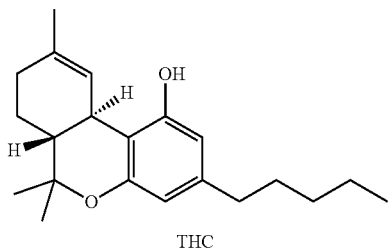

THC

Cannabidiol (CBD) outlined below has the systematic name 2-[1R-3-methyl-6R-(1-methylethenyl)-2-cyclohexen-1-yl]-5-pentyl-1,3-benzenediol or 2-[(6R)-3-methyl-6-prop-1-en-2-ylcyclohex-2-en-1-yl]-5-pentylbenzene-1,3-diol.

CBD is a non-psychoactive cannabinoid which preferentially binds to the type 2 cannabinoid receptor (CB2) and has been shown to have analgesic, anticonvulsive, antiemetic, anxiolytic, anti-oxidant, anti-psychotic properties, as well as utility as a muscle relaxant. CBD has a melting point of 62-63° C. and solubility of approximately 23.6 mg/mL in DSMO and ethanol.

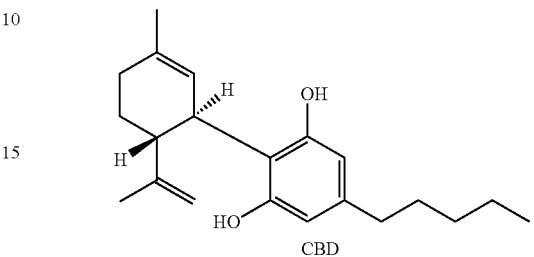

CBD

CBD has been demonstrated as an effective treatment of epilepsy in several clinical trials. In this regard, a product comprising pure CBD (Epidiolex®) was recently approved by the United States Food and Drug Administration (FDA). There are many un-approved (also not proven) medical uses of CBD-based products in forms such as oils, supplements, gums, as well as high concentration extracts available online for the treatment of various ailments.

It is known in the art that effects generated by CBD are different from those generated by THC. Indeed, the two compounds bind to different types of cannabinoid receptor as outlined above. THC has been shown to generate most of the effects which occur when CB1 is activated [1,2] including suppression of locomotor activity, hypothermia and antinociception. On the other hand, it has been shown that CBD generates effects on the heart rate or blood pressure under normal conditions. However, in animal models of stress, CBD reduces the heart rate and blood pressure [3,4].

In plant biosynthesis, THC and CBD are derived from their acidic precursors Δ9-tetrahydrocannabinolic acid (THCA) and cannabidiolic acid (CBDA). Decarboxylation of THCA and CBDA via light exposure, heating or aging results in THC or CBD.

Various studies have shown that CBD is unstable under acidic conditions. It was disclosed that under experimental conditions, heating CBD in acidic solution results in Δ-9-THC [5]. It was also disclosed that dissolving CBD in sulfuric acid/acetic acid yields a mixture of Δ-9-THC (52%) and Δ-8-THC (2%) [6]. U.S. 2004/0143126 discloses the conversion of CBD to Δ-9-THC under conditions involving $BF_3Et_2O$, a Lewis acid. It was reported that CBD converts to THC in human gut [7,6]. Indeed, the gastric fluid in the stomach has a pH of about 1.5.

CBD is also sensitive to alkaline conditions. For example, it has been reported that CBD converts to monomeric and dimeric hydroquinones under alkaline conditions [8]. Typically, the alkaline conditions involve the use of inorganic bases such as magnesium oxide, sodium carbonate, sodium bicarbonate, sodium hydrogen phosphate. Other inorganic bases including monopotassium phosphate, dipotassium phosphate, tripotassium phosphate, monosodium phosphate, disodium phosphate, trisodium phosphate, potassium bicarbonate and sodium bicarbonate are disclosed in U.S. 2015/0366906 in association with an alkaline drink. Organic bases are also used.

Under such alkaline conditions, both the micro pH (pH of the immediate environment surrounding the active ingredient) and the macro pH (pH of the environment where the active ingredient is dissolved) are controlled. However, due to the presence on the CBD molecule and other cannabinoid molecules, of highly reactive groups including the resorcinol group, the use of inorganic and organic bases in association therewith presents the risk of the occurrence of unwanted chemical side reactions [9-12 and U.S. 2011/0171295]. Also, inorganic and organic bases are known to be hydroscopic and thus present some challenges in maintaining the stability of formulations containing them. Nonetheless, the use of alkalizing agents is generally necessary, for example in order to enhance solubility in aqueous solutions, since CBD and other cannabinoids are highly lipophilic.

The use of *Cannabis* plant in various forms is known in the art. For example, U.S. 2004/0049059 discloses the use of *Cannabis* plant derivatives, such as marijuana to treat pain, nausea, appetite loss, epileptic seizures, multiple sclerosis symptoms and other disorders. U.S. Pat. No. 10,028,987 discloses *Cannabis*-infused milk, as an oral dosage form for pharmaceutical delivery of cannabinoids as a more palatable formulations for younger patients. U.S. Pat. No. 9,345,771 discloses oral formulation of THC comprising a mixture of ethanol and water. U.S. 2018/0020699 discloses cannabidiol-containing beverages comprising cannabidiol dissolved in water with an emulsifier and which is added to soft drinks. Mixtures of cannabinoids or *Cannabis* extracts enriched with CBD are also used and have shown to exhibit an activity that is superior to the activity obtained when CBD is used alone [13].

*Cannabis* is also administered by smoking, drinking (tea beverage), capsules, eating, suppositories or inhaling through a vaporizer. Smoking *Cannabis* provides quicker systemic effects. However, smoke may worsen or even cause respiratory conditions. In addition, there is a stigma associated with *Cannabis* smoking. Also, capsules and inhaling through a vaporizer would be difficult for people who have difficulty swallowing or inhaling such as in geriatric or younger populations.

There is still a need for products containing a cannabinoid and that present some stability. In particular, there is a need for products containing a cannabinoid and wherein unwanted side chemical reactions such as hydroquinones formation are avoided. Also, there is a need for such products presented in a form that is suitable for administration to all groups of people.

SUMMARY OF THE INVENTION

The inventors have designed and prepared an aqueous composition comprising a cannabinoid and an alkalizing agent which comprises pico size carbon particles. The cannabinoid may be CBD alone or in combination with other cannabinoids. For example, the cannabinoid may be a *Cannabis* extract enriched in CBD. The alkalizing agent comprising pico size carbon particles is present in the composition in an amount suitable for buffering the composition to a pH between about 7.5 and 9.5. The use of such alkalizing agent which is free of any inorganic or organic bases allows for the preparation of an alkaline aqueous composition which is stable and wherein unwanted chemical side reactions are avoided.

In embodiments of the invention, the aqueous composition is used in the preparation of a beverage. In other embodiments, the aqueous composition is used in the preparation of a pharmaceutical composition for medical administration to a patient.

In embodiments of the invention, the composition further comprises a sugar or polyol, preferably mannitol; a sweetener; a surfactant, preferably Tween® 80 or polysorbate 80; an emulsifier; a flavoring agent; a coloring agent; caffeine; an antioxidant; a vitamin; a probiotic; a mineral; or a combination thereof.

The invention thus provides the following in accordance with aspects thereof:

(1) An aqueous composition comprising a cannabinoid and an alkalizing agent which comprises pico size carbon particles.

(2) the aqueous composition according to (1) above, wherein the alkalizing agent comprising pico size carbon particles is present in an amount suitable for buffering the composition to a pH between about 7.5 to 9.5, about 7.5 to 9.0, about 7.5 to 8.5, about 7.5 to 8.0, about 8 to 9.5, about 8 to 9.0, about 8 to 8.5, or about 8.5 to 9.5, about 8.5 to 9.0.

(3) The aqueous composition according to (1) or (2) above, wherein the cannabinoid is present in an amount of about 1 to 100 mg/mL, about 10 to 100 mg/mL, about 20 to 100 mg/mL, about 30 to 100 mg/mL, about 35 to 100 mg/mL, about 40 to 100 mg/mL, about 45 to 100 mg/mL, about 50 to 100 mg/mL, about 55 to 100 mg/mL, about 60 to 100 mg/mL, or about 65 to 100 mg/mL.

(4) The aqueous composition according to any one of (1) to (3) above, wherein the cannabinoid is purified from a *Cannabis* extract or the cannabinoid is synthesized.

(5) The aqueous composition according to any one of (1) to (3) above, wherein the cannabinoid is a *Cannabis* extract enriched in cannabidiol (CBD).

(6) The aqueous composition according to any one of (1) to (5) above, wherein the cannabinoid comprises cannabidiol (CBD) and one or more of: tetrahydrocannabinol (Δ9-THC), cannabichromene (CBC), cannabigerol (CBG), cannabinol (CBN), and cannabidivarol (CBDV).

(7) The aqueous composition according to any one of (1) to (6) above, wherein the alkalizing agent is an oil-based material having pico size carbon particles suspended therein; optionally the oil-based material is Tall oil; optionally, the oil-based material is selected from the group consisting of hydrocarbon, higher fatty acid, higher alcohol, fatty acid ester of polyhydric alcohol, higher alcohol ether of polyhydric alcohol, polymer or copolymer of alkylene oxide, and a combination thereof.

(8) The aqueous composition according to any one of (1) to (7) above, wherein the pico size carbon particles are from an organic source.

(9) The aqueous composition according to any one of (1) to (8) above, further comprising a sugar or polyol, preferably the sugar is selected from the group consisting of mannitol, sucrose, glucose, fructose, high fructose corn syrup, invert syrup, refiner's syrup, corn syrup, maltose and high maltose syrups and mixtures thereof; more preferably the sugar or polyol is mannitol.

(10) The aqueous composition according to (9) above, wherein the sugar or polyol is present in an amount of about 2 to 20 mg/mL, about 3 to 20 mg/mL, about 4 to 20 mg/mL, about 5 to 20 mg/mL, about 6 to 20 mg/mL, about 7 to 20 mg/mL, or about 8 to 20 mg/mL.

(11) The aqueous composition according to (9) or (10) above, further comprising a sweetener which is artificial or from a natural source; optionally the sweetener is a non-calorie sweetener selected from the group consisting of aspartame, saccharine, stevia, cyclamates, acetosulfam, L-aspartyl-L-phenylalanine lower alkyl ester sweeteners, L-aspartyl-D-alanine amides, L-aspartyl-D-serine amides, L-aspartyl-hydroxymethylalkane amide, L-aspartyl-1-hydroxyethylalkane amide, and mixtures thereof.

(12) The aqueous composition according to any one of (1) to (11) above, further comprising a surfactant, preferably the surfactant is polysorbate 80 or Tween® 80.

(13) The aqueous composition according to (12) above, wherein the surfactant is present in an amount of about 1 to 30 mg/mL, about 2 to 30 mg/mL, about 3 to 30 mg/mL, about 4 to 30 mg/mL, about 5 to 30 mg/mL, about 6 to 30 mg/mL, about 7 to 30 mg/mL, about 8 to 30 mg/mL, about 9 to 30 mg/mL, about 10 to 30 mg/mL, about 11 to 30 mg/mL, or about 12 to 30 mg/mL.

(14) The aqueous composition according to any one of (1) to (13) above, further comprising an ingredient selected from the group consisting of an emulsifier, a flavor agent which is artificial or from a natural source, a coloring agent which is artificial or from a natural source, caffeine, an antioxidant, a vitamin, a probiotic, a mineral, and a combination thereof.

(15) The aqueous composition according to any one of (1) to (14) above, which is stable for a period of at least about 24 months.

(16) The aqueous composition according to any one of (1) to (15) above, which is suitable for human consumption.

(17) The aqueous composition according to any one of (1) to (15) above, which is suitable for medical administration to a patient in need of cannabinoid.

(18) The aqueous composition according to any one of (1) to (17) above, wherein the cannabinoid is cannabidiol (CBD).

(19) The aqueous composition according to any one of (1) to (18) above, wherein the cannabinoid comprises a salt of the cannabinoid.

(20) An aqueous composition comprising cannabidiol (CBD) and an alkalizing agent which comprises pico size carbon particles.

(21) The aqueous composition according to (20) above, wherein the alkalizing agent comprising pico size carbon particles is present in an amount suitable for buffering the composition to a pH between about 7.5 to 9.5, about 7.5 to 9.0, about 7.5 to 8.5, about 7.5 to 8.0, about 8 to 9.5, about 8 to 9.0, about 8 to 8.5, or about 8.5 to 9.5, about 8.5 to 9.0.

(22) The aqueous composition according to (20) or (21) above, wherein CBD is present in an amount of about 1 to 100 mg/mL, about 10 to 100 mg/mL, about 20 to 100 mg/mL, about 30 to 100 mg/mL, about 35 to 100 mg/mL, about 40 to 100 mg/mL, about 45 to 100 mg/mL, about 50 to 100 mg/mL, about 55 to 100 mg/mL, about 60 to 100 mg/mL, or about 65 to 100 mg/mL.

(23) The aqueous composition according to any one of (20) to (22) above, wherein CBD is purified from a *Cannabis* extract or CBD is synthesized.

(24) The aqueous composition according to any one of (20) to (23) above, wherein the alkalizing agent is an oil-based material having pico size carbon particles suspended therein; optionally the oil-based material is Tall oil; optionally, the oil-based material is selected from the group consisting of hydrocarbon, higher fatty acid, higher alcohol, fatty acid ester of polyhydric alcohol, higher alcohol ether of polyhydric alcohol, polymer or copolymer of alkylene oxide, and a combination thereof.

(25) A beverage comprising the aqueous composition as defined in any one of (1) to (24) above; optionally the beverage is a carbonated beverage.

(26) A pharmaceutical composition comprising the aqueous composition as defined in any one of (1) to (24) above; optionally the pharmaceutical composition comprises a pharmaceutically acceptable carrier or excipient.

(27) A pharmaceutical composition comprising a cannabinoid, an alkalizing agent which comprises pico size carbon particles, and water.

(28) The pharmaceutical composition according to (27) above, which has a pH between about 7.5 to 9.5, about 7.5 to 9.0, about 7.5 to 8.5, about 7.5 to 8.0, about 8 to 9.5, about 8 to 9.0, about 8 to 8.5, or about 8.5 to 9.5, about 8.5 to 9.0.

(29) The pharmaceutical composition according to (27) or (28) above, wherein the cannabinoid is present in an amount of about 1 to 100 mg/mL, about 10 to 100 mg/mL, about 20 to 100 mg/mL, about 30 to 100 mg/mL, about 35 to 100 mg/mL, about 40 to 100 mg/mL, about 45 to 100 mg/mL, about 50 to 100 mg/mL, about 55 to 100 mg/mL, about 60 to 100 mg/mL, or about 65 to 100 mg/mL.

(30) The pharmaceutical composition according to any one of (27) to (29) above, wherein the cannabinoid is purified from a *Cannabis* extract or the cannabinoid is synthesized.

(31) The pharmaceutical composition according to any one of (27) to (30) above, wherein the cannabinoid is a *Cannabis* extract enriched in cannabidiol (CBD).

(32) The pharmaceutical composition according to any one of (27) to (31) above, wherein the cannabinoid comprises cannabidiol (CBD) and one or more of: tetrahydrocannabinol (Δ9-THC), cannabichromene (CBC), cannabigerol (CBG), cannabinol (CBN), and cannabidivarol (CBDV).

(33) The pharmaceutical composition according to any one of (27) to (32) above, wherein the alkalizing agent is an oil-based material having pico size carbon particles suspended therein; optionally, the oil-based material is selected from the group consisting of hydrocarbon, higher fatty acid, higher alcohol, fatty acid ester of polyhydric alcohol, higher alcohol ether of polyhydric alcohol, polymer or copolymer of alkylene oxide, and a combination thereof.

(34) A pharmaceutical composition comprising cannabidiol (CBD), an alkalizing agent which comprises pico size carbon particles, and water.

(35) The pharmaceutical composition according to (34) above, wherein the alkalizing agent comprising pico size carbon particles is present in an amount suitable for buffering the composition to a pH between about 7.5 to 9.5, about 7.5 to 9.0, about 7.5 to 8.5, about 7.5 to 8.0, about 8 to 9.5, about 8 to 9.0, about 8 to 8.5, or about 8.5 to 9.5, about 8.5 to 9.0.

(36) The pharmaceutical composition according to (34) or (35) above, wherein CBD is present in an amount of about 1 to 100 mg/mL, about 10 to 100 mg/mL, about 20 to 100 mg/mL, about 30 to 100 mg/mL, about 35 to 100 mg/mL, about 40 to 100 mg/mL, about 45 to 100 mg/mL, about 50 to 100 mg/mL, about 55 to 100 mg/mL, about 60 to 100 mg/mL, or about 65 to 100 mg/mL.

(37) The pharmaceutical composition according to any one of (34) to (36) above, wherein CBD is purified from a *Cannabis* extract or CBD is synthesized.

(38) The pharmaceutical composition according to any one of (34) to (37) above, wherein the alkalizing agent is an oil-based material having pico size carbon particles suspended therein; optionally the oil-based material is Tall oil; optionally, the oil-based material is selected from the group consisting of hydrocarbon, higher fatty acid, higher alcohol, fatty acid ester of polyhydric alcohol, higher alcohol ether of polyhydric alcohol, polymer or copolymer of alkylene oxide, and a combination thereof.

(39) The pharmaceutical composition according to any one of (34) to (38) above, further comprising a pharmaceutically acceptable carrier.

(40) A method of preparing an aqueous composition comprising a cannabinoid, the method comprising:
(a) providing the cannabinoid;
(b) providing an alkalizing agent which comprises pico size carbon particles;
(c) mixing the cannabinoid and the alkalizing agent and stirring the mixture for a period of time; and
(d) adding water to the mixture for a period of time to obtain the aqueous composition.

(41) The method according to (40) above, wherein step (a) comprises one or more of:
(a1) extracting the cannabinoid from a *Cannabis* extract;
(a2) submitting a *Cannabis* extract to a cannabidiol (CBD)-enriched process to obtain a *Cannabis* extract enriched with CBD; and
(a3) providing a mixture of CBD with one or more of tetrahydrocannabinol THC), cannabichromene (CBC), cannabigerol (CBG), cannabinol (CBN), and cannabidivarol (CBDV).

(42) The method according to (40) or (41) above, wherein step (b) comprises providing an oil-based material having pico size carbon particles suspended therein; optionally the oil-based material is tall oil.

(43) The method according to any one of (40) to (42) above, wherein step (c) is performed at room temperature and/or the mixture is stirred for about 30 minutes.

(44) The method according to any one of (40) to (43) above, wherein at step (d) the mixture is stirred for about 30 minutes.

(45) The method according to any one of (40) to (44) above, further comprising storing the aqueous alkaline composition for future use.

(46) The method according to any one of (40) to (45) above, wherein the aqueous composition has a pH between about 7.5 to 9.5, about 7.5 to 9.0, about 7.5 to 8.5, about 7.5 to 8.0, about 8 to 9.5, about 8 to 9.0, about 8 to 8.5, or about 8.5 to 9.5, about 8.5 to 9.0.

(47) The method according to any one of (40) to (46) above, wherein the cannabinoid is present in an amount of about 1 to 100 mg/mL, about 10 to 100 mg/mL, about 20 to 100 mg/mL, about 30 to 100 mg/mL, about 35 to 100 mg/mL, about 40 to 100 mg/mL, about 45 to 100 mg/mL, about 50 to 100 mg/mL, about 55 to 100 mg/mL, about 60 to 100 mg/mL, or about 65 to 100 mg/mL.

(48) The method according to any one of (40) to (47) above, wherein the alkalizing agent is an oil-based material having pico size carbon particles suspended therein; optionally the oil-based material is Tall oil; optionally, the oil-based material is selected from the group consisting of hydrocarbon, higher fatty acid, higher alcohol, fatty acid ester of polyhydric alcohol, higher alcohol ether of polyhydric alcohol, polymer or copolymer of alkylene oxide, and a combination thereof.

(49) The method according to any one of (40) to (48) above, wherein the cannabinoid is cannabidiol (CBD).

(50) A method of preparing an aqueous composition comprising cannabidiol (CBD), the method comprising:
(a) providing CBD;
(b) providing an alkalizing agent which comprises pico size carbon particles;
(c) mixing CBD and the alkalizing agent and stirring the mixture for a period of time; and
(d) adding water to the mixture for a period of time to obtain the aqueous composition.

(51) A method of treating a patient in need of a cannabinoid, comprising administering to the patient a pharmaceutical composition as defined in any one of (26) to (39) above.

(52) A method of treating a patient in need of a cannabinoid, comprising administering to the patient a pharmaceutical composition comprising a cannabinoid, an alkalizing agent which comprises pico size carbon particles, and water.

(53) A method of treating a patient in need of cannabidiol (CBD), comprising administering to the patient a pharmaceutical composition comprising CBD, an alkalizing agent which comprises pico size carbon particles, and water.

(54) Use of a pharmaceutical composition as defined in any one of (26) to (39) above, for treating a patient in need of a cannabinoid.

(55) Use of a pharmaceutical composition comprising a cannabinoid, an alkalizing agent which comprises pico size carbon particles, and water, for treating a patient in need of a cannabinoid.

(56) Use of a pharmaceutical composition comprising a cannabinoid, an alkalizing agent which comprises pico size carbon particles, and water, in the manufacture of a medicament for treating a patient in need of cannabinoid.

(57) The use of (56) above, wherein the medicament is suitable for oral administration, for injection, for administration by spraying, or for administration by pumping.

(58) The use according to any one of (55) to (57) above, wherein the cannabinoid is cannabidiol (CBD).

(59) The pharmaceutical composition according to any one of (26) to (39) above, for use in the treatment of a patient in need of cannabinoid.

(60) The aqueous composition according to any one of (1) to (24) above, for use in the preparation of a beverage.

(61) A kit comprising:
a cannabinoid;
an alkalizing agent which comprises pico size carbon particles;
water; and
instructions for use.

(62) A kit comprising:
cannabidiol (CBD);
an alkalizing agent which comprises pico size carbon particles;
water; and
instructions for use.

(63) A kit comprising:
a mixture comprising cannabidiol (CBD) and an alkalizing agent which comprises pico size carbon particles, optionally the mixture is suspended in an emulsifier;
water; and
instructions for use.

(64) The kit according to any one of (61) to (63) above, wherein the use is for the preparation of a medicament or for the preparation of a beverage.

Other objects, advantages and features of the present invention will become more apparent upon reading of the following non-restrictive description of specific embodiments thereof, given by way of example only with reference to the accompanying drawings.

BRIEF DESCRIPTION OF THE DRAWINGS

In the appended drawings.

DESCRIPTION OF ILLUSTRATIVE EMBODIMENTS

Figure 1:
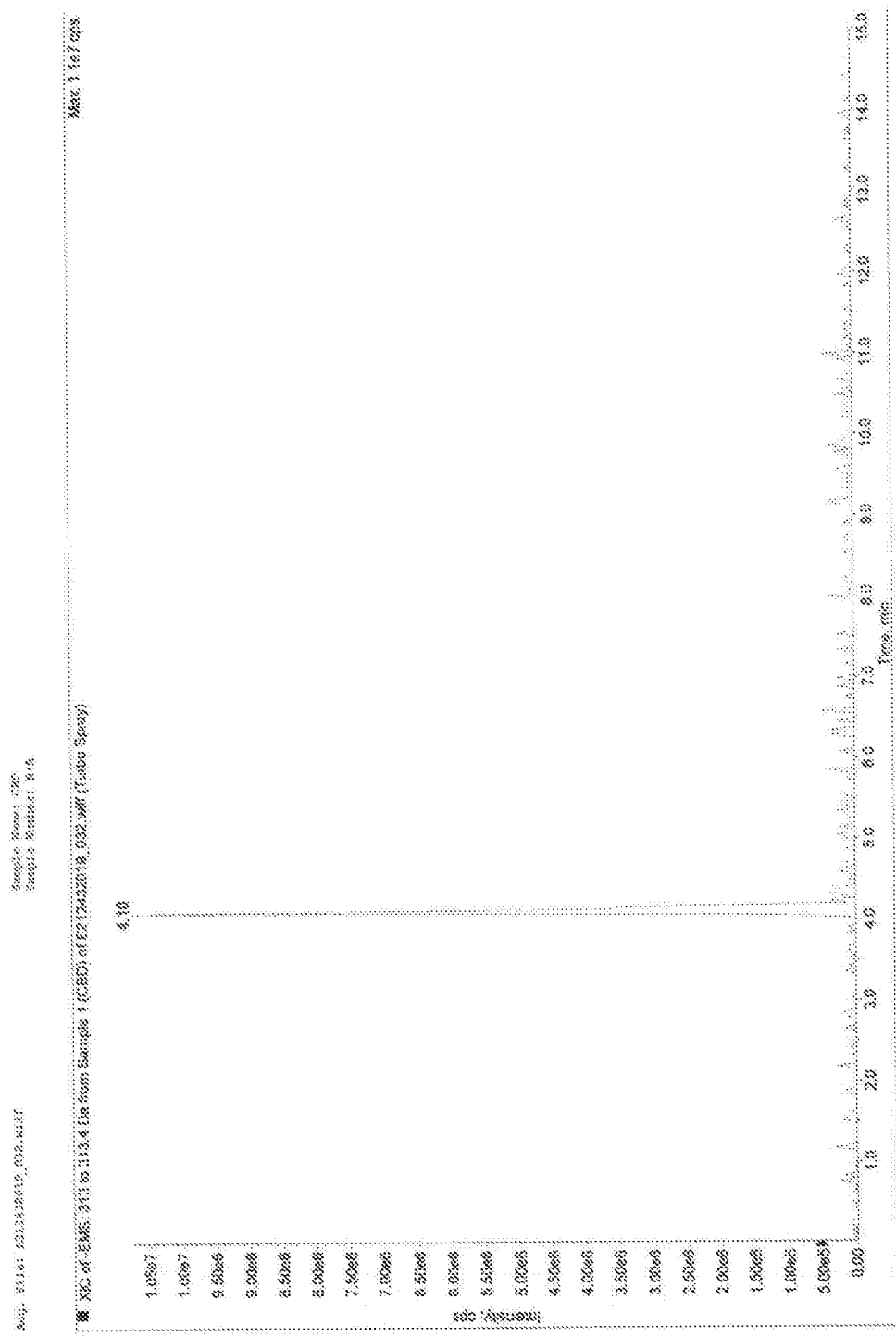
FIG. 1: Extracted Ion Chromatogram (EIC) (m/z 313) of CBD oil.

Before the present invention is further described, it is to be understood that the invention is not limited to the particular embodiments described below, as variations of these embodiments may be made and still fall within the scope of the appended claims. It is also to be understood that the terminology employed is for the purpose of describing particular embodiments; and is not intended to be limiting. Instead, the scope of the present invention will be established by the appended claims.

In order to provide a clear and consistent understanding of the terms used in the present specification, a number of definitions are provided below. Moreover, unless defined otherwise, all technical and scientific terms as used herein have the same meaning as commonly understood to one of ordinary skill in the art to which this disclosure pertains.

Use of the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

As used herein when referring to numerical values or percentages, the term "about" includes variations due to the methods used to determine the values or percentages, statistical variance and human error. Moreover, each numerical parameter in this application should at least be construed in light of the number of reported significant digits and by applying ordinary rounding techniques.

As used herein, the term "pico size carbon particles" refers to carbon particles having an average size of about $1 \times 10^{-12}$ m.

As used herein, the term "alkalizing agent" refers to an ingredient used in the composition according to the invention and which is suitable for buffering the composition to a pH of between about 7.5 to 9.5. In embodiments of the invention, such alkalizing agent comprises pico size carbon particles as defined above.

The inventors have designed and prepared a stable alkaline aqueous composition comprising a cannabinoid. The cannabinoid in the composition according to the invention may be purified from a *Cannabis* extract or synthesized. The cannabinoid in the composition according to the invention comprises cannabidiol (CBD), used alone or in combination with other cannabinoids. For example, the cannabinoid may be a *Cannabis* extract enriched in CBD. Other cannabinoids used with CBD may be for example tetrahydrocannabinol (Δ9-THC), cannabichromene (CBC), cannabigerol (CBG), cannabinol (CBN), and cannabidivarol (CBDV). In embodiments of the invention, the cannabinoid is present in an amount of about 1 to 100 mg/mL, about 10 to 100 mg/mL, about 20 to 100 mg/mL, about 30 to 100 mg/mL, about 35 to 100 mg/mL, about 40 to 100 mg/mL, about 45 to 100 mg/mL, about 50 to 100 mg/mL, about 55 to 100 mg/mL, about 60 to 100 mg/mL, or about 65 to 100 mg/mL.

The composition according to the invention comprises an alkalizing agent. Such alkalizing agent comprises pico size carbon particles and is used in an amount suitable for buffering the composition to a pH of between about 7.5 to 9.5, about 7.5 to 9.0, about 7.5 to 8.5, about 7.5 to 8.0, about 8 to 9.5, about 8 to 9.0, about 8 to 8.5, or about 8.5 to 9.5, about 8.5 to 9.0. In embodiments of the invention, the alkalizing agent may be an oil-based material having pico size carbon particles suspended therein. The oil-based material may comprise Tall oil or the oil-based material may comprise a material selected from the group consisting of hydrocarbon, higher fatty acid, higher alcohol, fatty acid ester of polyhydric alcohol, higher alcohol ether of polyhydric alcohol, polymer or copolymer of alkylene oxide, and a combination thereof. The oil-based material may comprise any suitable oil-based material known in the art as disclosed for example in EP 0546358B1. In other embodiments of the invention, the pico size carbon particles may be from an organic source.

As will be understood by a skilled person, the alkalizing agent according to the invention is selected such as to avoid unwanted chemical side reactions with the cannabinoid; for example, such as to avoid the formation of hydroquinones.

In embodiments of the invention, a beverage comprising the alkaline aqueous composition according to the invention is provided. Suitable forms and other ingredients of such beverage are described herein below.

In embodiments of the invention, a pharmaceutical composition comprising the alkaline aqueous composition according to the invention is provided. The pharmaceutical composition may further comprise a pharmaceutically acceptable carrier or excipient. In embodiments of the invention, the alkaline aqueous composition is used in the preparation of a medicament for treating a patient in need of a cannabinoid. Also, the invention relates to a method of treating a patient in need of a cannabinoid, the method comprising using the aqueous alkaline composition or the pharmaceutical composition or the medicament according to the invention.

In embodiments of the invention, a kit is provided which may be used in the preparation of the aqueous alkaline composition or the pharmaceutical composition or the medicament according to the invention. The kit may comprise the cannabinoid, the alkalizing agent, water, and instructions for proceeding. In other embodiments of this aspect of the invention, sachets (little packages) may be provided, which content a mixture of cannabinoid (CBD) oil and pico size carbon particles, and the mixture is dissolved in water prior to consumption. The mixture may further comprise an emulsifier or other suitable ingredients.

In embodiments of the invention, a method of preparing the alkaline aqueous composition according to the invention is provided. The method comprises providing the cannabinoid or CBD-enriched cannabinoid mixture as described herein. Also, the method comprises providing the alkalizing agent comprising pico size carbon particles as described herein. The cannabinoid and the alkalizing agent are then mixed in the presence of water as described in the example below.

Example 1—Preparation of the Composition According to the Invention

Figure 2:
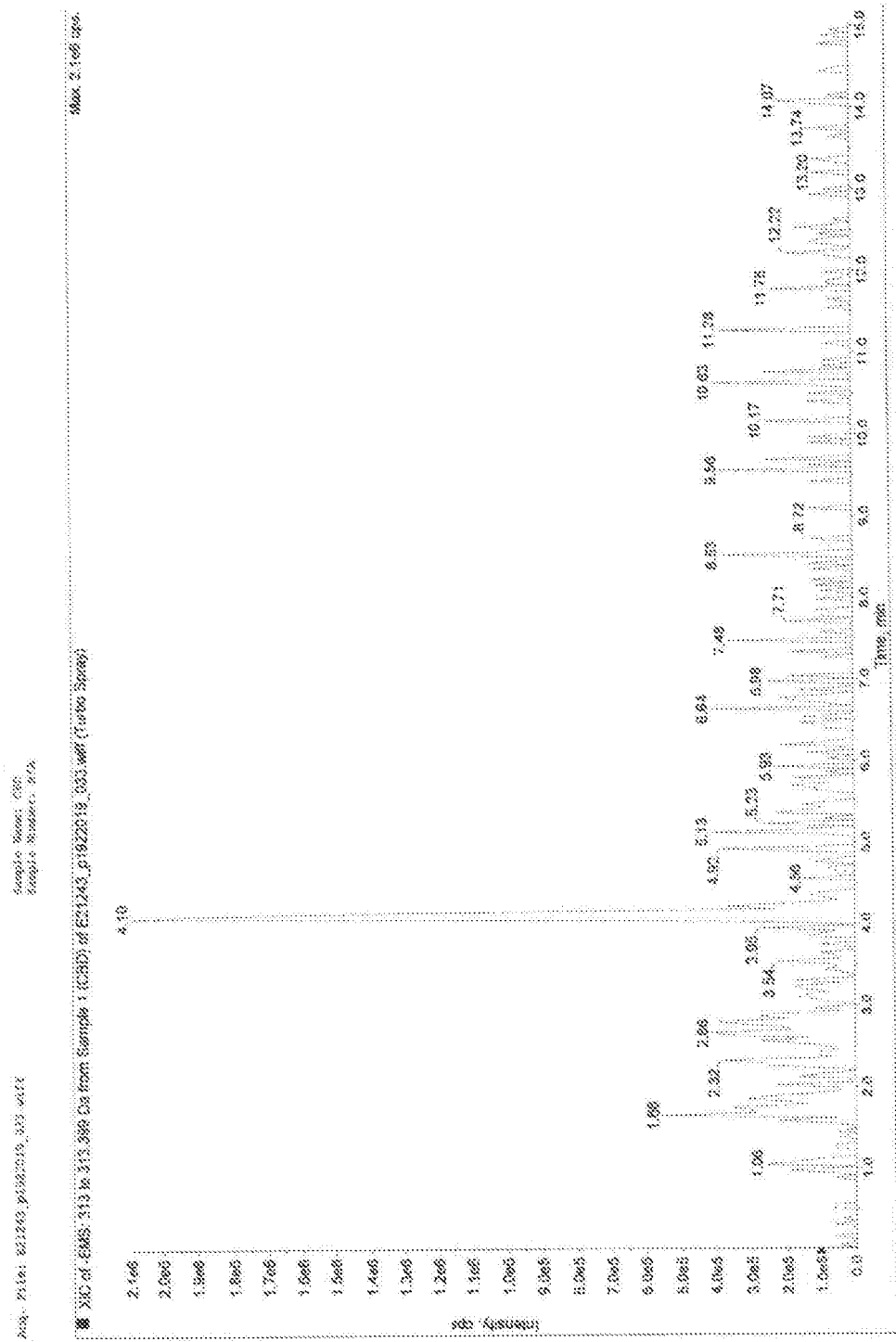
FIG. 2: Extracted Ion Chromatogram (EIC) (m/z 313) of CBD oil in pico size carbon particles suspended in Tall oil, Tween 80 and water.

10 µL of CBD oil (10.98 mg) was mixed with 20 µL of pico size carbon particles (40.77 mg) suspended in Tall oil to give a light yellow, clear solution with a pH of 8.24. This solution was added to 250 mL of water comprising 75.15 mg of Tween 80. This mixture was stirred well at room temperature for half an hour to give a clear solution with a pH of 8.96. Degradation of cannabidiol to monomeric or dimeric hydroquinones not observed. This can be seen in FIG. 2 which is the Extracted Ion Chromatogram (EIC) (m/z 313) of the mixture obtained. Reference FIG. 1 is which is the EIC (m/z 313) of CBD oil.

As described herein, the aqueous alkaline composition of the present invention may comprise sugars. The term "sugar" refers to both mono- and di-saccharides. Examples of sugars include sucrose, glucose, fructose, high fructose corn syrup, invert syrup, refiner's syrup, corn syrup, maltose and high maltose syrups and mixtures thereof. Preferred sugars are sucrose and high fructose corn syrup. Artificial sweeteners may also be used. It is known in the art that gums, pectins and other thickeners are generally used with artificial sweeteners to act as bulking agents and provide texture to the product. Mixtures comprising sugars and artificial sweeteners may be used.

In embodiments of the invention wherein the composition is presented as diet beverages, non-caloric sweeteners may be used. Examples of non-calorie sweeteners include aspartame, saccharine, stevia, cyclamates, acetosulfam, L-aspartyl-L-phenylalanine lower alkyl ester sweeteners, L-aspartyl-D-alanine amides as disclosed in U.S. Pat. No. 4,411,925, L-aspartyl-D-serine amides disclosed in U.S. Pat. No. 4,399,163, L-aspartyl-hydroxymethylalkane amide sweeteners disclosed in U.S. Pat. No. 4,338,346, L-aspartyl-1-hydroxyethylalkane amide sweeteners disclosed in U.S. Pat. No. 4,423,029, glycerin, synthetic alkoxy aromatics, and the like.

The aqueous alkaline composition of the present invention may comprise flavoring agents. Such flavoring agents may be natural or artificial, and selected from fruit flavors, botanical flavors and mixtures thereof. For example, fruit flavors include, apples, oranges, lemon, limes, etc. Also included within the term fruit flavor are synthetically prepared flavors made to simulate fruit flavors derived from natural sources. Particularly preferred fruit flavors are the citrus flavors including orange, lemon, lime and grapefruit flavors. A variety of other fruit flavors can be used such as apple, grape, cherry, pineapple, coconut and the like. These fruit flavors may be derived from natural sources such as fruit juices and flavor oils or synthetically prepared. As used herein, the term botanical flavor refers to flavors derived from parts of the plant other than the fruit. As such, botanical flavors can include those flavors derived from nuts, bark, roots and leaves. Examples of such botanical flavors include cola flavors, tea flavors, coffee and the like.

The aqueous alkaline composition of the present invention may further comprise a food grade antioxidant in an amount sufficient to inhibit oxidation of cannabidiol. Excessive oxidation can contribute to the degradation of cannabidiol to monomeric and dimeric hydroxyquinones. Known or conventional food grade antioxidants can be used. Such food grade antioxidants include, but are not limited to, butylated hydroxyanisole (BHA), butylated hydroxytoluene (BHT), and mixtures thereof. Selection of an effective amount of a food grade antioxidant is easily determined by the skilled person. Limitations on such amounts or concentrations are normally subject to government regulations.

The aqueous alkaline composition of the present invention may comprise an emulsifier. Emulsifiers may include gums, pectins, cellulose, polysorbates, sorbitan esters and propylene glycol alginates.

In embodiments of the aqueous alkaline composition of the present invention, caffeine may be added to the composition. If necessary, coloring agents may also be added beverages according to the present invention. Any suitable soluble coloring agents approved for food use may be utilized for the present invention.

In embodiments of the invention, beverages may be carbonated e.g., flavored seltzer waters, soft drinks or mineral drinks, as well as non-carbonated juices, punches and concentrated forms. By way of example, the juices used herein include grape, pear, passion fruit, pineapple, banana or banana puree, apricot, orange, lemon, grapefruit, apple, cranberry, tomato, mango, papaya, lime, tangerine, cherry, raspberry, melon, carrot, cabbage, celery, cucumber, spinach, tomato, and mixtures thereof. Additionally, artificial flavors, e.g. cola, or natural flavors derived from these juices may be used in the composition. Chocolate flavors and other non-fruit flavors may also be used in the composition. Also, beverages according to the invention may comprise a vitamin, a probiotic and/or a mineral.

In embodiments of the invention, the aqueous alkaline composition is packaged into glass or plastic bottles, or other suitable containers. Preferably, the plastic material of the bottle is amber colored and with an oxygen-impermeable barrier which are commercially available and will be known to persons skilled in the art.

The scope of the claims should not be limited by the preferred embodiments set forth in the examples; but should be given the broadest interpretation consistent with the description as a whole.

The present description refers to a number of documents, the content of which is herein incorporated by reference in their entirety.

REFERENCES

1. Pertwee, R. The diverse CB1 and CB2 receptor pharmacology of three plant cannabinoids: Δ9-tetrahydrocannabinol, cannabidiol and Δ9-tetrahydrocannabivarin. *British Journal of pharmacology* (2008), 153(2), 199-215.
2. Long, L. E. et al. A behavioral comparison of acute and chronic Δ9-tetrahydrocannabinol and cannabidiol in C57BL/6JArc mice. *International Journal of Neuropsychopharmacology* (2010), 13(7), 861-876.
3. Batalla, A. et al. Neuroimaging studies of acute effects of THC and CBD in humans and animals: a systematic review. *Current Pharmaceutical Design* (2014), 20(13), 2168-2185
4. Sultan, S. R. et al. A systematic review and meta-analysis of the haemodynamic effects of Cannabidiol. *Frontiers in Pharmacology* (2017), 8, 81.
5. Gaoni, Y. and R. Mechoulam, Hashish-VII. The isomerization of cannabidiol to tetrahydrocannabinols (1966), 22, 1481-1488.
6. Watanabe, K. et al. Conversion of cannabidiol to Δ9-tetrahydrocannabinol and related cannabinoids in artificial gastric juice, and their pharmacological effects in mice. *Forensic Toxicology* (2007), 25(1), 16-21.
7. Merrick, J. et al. Identification of psychoactive degradants of cannabidiol in simulated gastric and physiological fluid. *Cannabis and Cannabinoid Research* (2016), 1(1), 102-112.
8. Trofin, I. G. Long term storage and *Cannabis* oil stability. *Revista De Chemie* (2012), 63(3), 293-297.
9. Nguyen et al. Enhanced gastric stability of esomeprazole by molecular interaction and modulation of microenvironmental pH with alkalizers in solid dispersion, *International Journal of Pharmaceutics* (2017), 523, 189-202.
10. Benetti et al. Esomeprazole immediate release tablets: Gastric mucosa ex vivo permeation, absorption and antisecretory activity in conscious rats, *Journal of Controlled Release* (2016), 238, 203-210.
11. Dressman et al. Improving drug solubility for oral delivery suing solid dispersions, *European Journal of Pharmaceutics and Biopharmaceutics* (2000), 50, 47-60.
12. Park et al. Modulation of microenvironmental pH and utilization of alkalizers in crystalline solid dispersion for enhanced solubility and stability of clarithromycin, *Acrh. Pharm. Res.* (2015), 38, 839-848.
13. Gallily et al. Overcoming the bell-shaped dose-response of cannabidiol by using *Cannabis* extract enriched in cannabidiol, *Pharmacology & Pharmacy* (2015), 6, 75-85.

The invention claimed is:

1. An aqueous composition comprising a cannabinoid and an alkalizing agent which comprises pico size carbon particles.

2. The aqueous composition according to claim 1, wherein the alkalizing agent comprising pico size carbon particles is present in an amount suitable for buffering the composition to a pH between about 7.5 to 9.5, about 7.5 to 9.0, about 7.5 to 8.5, about 7.5 to 8.0, about 8 to 9.5, about 8 to 9.0, about 8 to 8.5, or about 8.5 to 9.5, about 8.5 to 9.0.

3. The aqueous composition according to claim 1, wherein the cannabinoid is present in an amount of about 1 to 100 mg/mL, about 10 to 100 mg/mL, about 20 to 100 mg/mL, about 30 to 100 mg/mL, about 35 to 100 mg/mL, about 40 to 100 mg/mL, about 45 to 100 mg/mL, about 50 to 100 mg/mL, about 55 to 100 mg/mL, about 60 to 100 mg/mL, or about 65 to 100 mg/mL.

4. The aqueous composition according to claim 1, wherein the cannabinoid is purified from a *Cannabis* extract, or the cannabinoid is synthesized, or the cannabinoid is a *Cannabis* extract enriched in cannabidiol (CBD).

5. The aqueous composition according to claim 1, wherein the cannabinoid comprises cannabidiol (CBD) and one or more of: tetrahydrocannabinol ($\Delta$9-THC), cannabichromene (CBC), cannabigerol (CBG), cannabinol (CBN), and cannabidivarol (CBDV).

6. The aqueous composition according to claim 1, wherein the alkalizing agent is an oil-based material having pico size carbon particles suspended therein; optionally the oil-based material is Tall oil; optionally, the oil-based material is selected from the group consisting of hydrocarbon, higher fatty acid, higher alcohol, fatty acid ester of polyhydric alcohol, higher alcohol ether of polyhydric alcohol, polymer or copolymer of alkylene oxide, and a combination thereof.

7. The aqueous composition according to claim 1, wherein the pico size carbon particles are from an organic source.

8. The aqueous composition according to claim 1,
further comprising a sugar or polyol, optionally the sugar is selected from the group consisting of mannitol, sucrose, glucose, fructose, high fructose corn syrup, invert syrup, refiner's syrup, corn syrup, maltose and high maltose syrups and mixtures thereof; optionally the sugar or polyol is mannitol; and optionally the sugar or polyol is present in an amount of about 2 to 20 mg/mL, about 3 to 20 mg/mL, about 4 to 20 mg/mL, about 5 to 20 mg/mL, about 6 to 20 mg/mL, about 7 to 20 mg/mL, or about 8 to 20 mg/mL; and/or further comprising a sweetener which is artificial or from a natural source; optionally the sweetener is a non-calorie sweetener selected from the group consisting of aspartame, saccharine, stevia, cyclamates, acetosulfam, L-aspartyl-L-phenylalanine lower alkyl ester sweeteners, L-aspartyl-D-alanine amides, L-aspartyl-D-serine amides, L-aspartyl-hydroxymethylalkane amide, L-aspartyl-1-hydroxyethylalkane amide, and mixtures thereof; and/or further comprising a surfactant, optionally the surfactant is polysorbate 80 or Tween® 80; and optionally the surfactant is present in an amount of about 1 to 30 mg/mL, about 2 to 30 mg/mL, about 3 to 30 mg/mL, about 4 to 30 mg/mL, about 5 to 30 mg/mL, about 6 to 30 mg/mL, about 7 to 30 mg/mL, about 8 to 30 mg/mL, about 9 to 30 mg/mL, about 10 to 30 mg/mL, about 11 to 30 mg/mL, or about 12 to 30 mg/mL; and/or further comprising an ingredient selected from the group consisting of an emulsifier, a flavor agent which is artificial or from a natural source, a coloring agent which is artificial or from a natural source, caffeine, an antioxidant, a vitamin, a probiotic, a mineral, and a combination thereof.

9. The aqueous composition according to claim 1, which is stable for a period of at least about 24 months.

10. The aqueous composition according to claim 1, which is suitable for human consumption, and/or which is suitable for medical administration to a patient in need of cannabinoid.

11. The aqueous composition according to claim 1, wherein the cannabinoid is cannabidiol (CBD).

12. The aqueous composition according to claim 1, wherein the cannabinoid comprises a salt of the cannabinoid.

13. A beverage comprising the aqueous composition as defined in claim 1; optionally the beverage is a carbonated beverage.

14. A pharmaceutical composition comprising the aqueous composition as defined in claim 1; optionally the pharmaceutical composition comprises a pharmaceutically acceptable carrier or excipient.

15. A method of preparing the aqueous composition as defined in claim 1, the method comprising:
(a) providing the cannabinoid;
(b) providing an alkalizing agent which comprises pico size carbon particles;
(c) mixing the cannabinoid and the alkalizing agent and stirring the mixture for a period of time; and
(d) adding water to the mixture for a period of time to obtain the aqueous composition, optionally the cannabinoid is cannabidiol (CBD).

16. The method according to claim 15, wherein step (a) comprises one or more of:
(a1) extracting the cannabinoid from a *Cannabis* extract;
(a2) submitting a *Cannabis* extract to a cannabidiol (CBD)-enriched process to obtain a *Cannabis* extract enriched with CBD; and
(a3) providing a mixture of CBD with one or more of tetrahydrocannabinol ($\Delta$9-THC), cannabichromene (CBC), cannabigerol (CBG), cannabinol (CBN), and cannabidivarol (CBDV).

17. The method according to claim 15, wherein:
step (b) comprises providing an oil-based material having pico size carbon particles suspended therein; optionally the oil-based material is tall oil; and/or
step (c) is performed at room temperature and/or the mixture is stirred for about 30 minutes; and/or at step (d) the mixture is stirred for about 30 minutes; and/or the method further comprises storing the aqueous alkaline composition for future use.

18. A method of treating a patient in need of a cannabinoid, comprising administering to the patient a pharmaceutical composition comprising a cannabinoid, an alkalizing agent which comprises pico size carbon particles, and water; optionally the cannabinoid is cannabidiol (CBD).

19. A kit comprising:
- a cannabinoid;
- an alkalizing agent which comprises pico size carbon particles;
- water; and
- instructions for use, optionally the cannabinoid is cannabidiol (CBD), and/or optionally the cannabinoid and the alkalizing agent are suspended in an emulsifier.

20. The kit according to claim 19, wherein the use is for the preparation of a medicament or for the preparation of a beverage.

* * * * *